United States Patent [19]

Kasai

[11] Patent Number: 5,033,476
[45] Date of Patent: Jul. 23, 1991

[54] BLOOD COLLECTING TUBE
[75] Inventor: Masaaki Kasai, Fuji, Japan
[73] Assignee: Terumo Kabushiki Kaisha, Tokyo, Japan
[21] Appl. No.: 378,185
[22] PCT Filed: Jun. 18, 1987
[86] PCT No.: PCT/JP87/00400
§ 371 Date: Aug. 4, 1989
§ 102(e) Date: Aug. 4, 1989
[87] PCT Pub. No.: WO88/04154
PCT Pub. Date: Jun. 16, 1988

[30] Foreign Application Priority Data
Dec. 11, 1986 [JP] Japan .................. 61-189842[U]
[51] Int. Cl.$^5$ .................................. A61B 5/00
[52] U.S. Cl. ..................... 128/764; 128/763; 604/411; 604/413; 604/415
[58] Field of Search ............... 128/763, 764; 604/403, 604/411–415

[56] References Cited
U.S. PATENT DOCUMENTS

| | | | |
|---|---|---|---|
| 3,987,791 | 10/1976 | Chittenden et al. ............... | 604/413 |
| 4,349,035 | 9/1982 | Thomas et al. ................... | 604/413 X |
| 4,420,517 | 12/1983 | Ali ................................... | 604/403 X |
| 4,559,052 | 12/1985 | Babson ............................ | 604/415 X |
| 4,808,381 | 2/1989 | McGregor et al. ............... | 604/411 X |
| 4,813,426 | 3/1989 | Haber et al. ..................... | 128/763 |
| 4,856,533 | 8/1989 | Anraku et al. ................... | 128/763 |
| 4,863,453 | 9/1989 | Berger et al. .................... | 604/415 |
| 4,920,976 | 5/1990 | Calzi et al. ...................... | 128/764 |

FOREIGN PATENT DOCUMENTS
1388494 3/1975 United Kingdom .

Primary Examiner—Robert A. Hafer
Assistant Examiner—Kerry Owens
Attorney, Agent, or Firm—Frishauf, Holtz, Goodman & Woodward

[57] ABSTRACT

The blood collecting tube of the present invention has a tubular body that is opened at one end and closed at the other end and a sealing member which is bonded to the peripheral edge of the opening of the tubular body so as to seal this opening. Also, the blood collecting tube of the present invention has a tubular body that is opened at one end and is closed at the other end and a sealing member which can be pierced by a hollow needle and is bonded to peripheral edge of the opening of the tubular body to seal the opening in which the internal pressure of the tubular body is suitable reduced in accordance with the amount of blood to be collected, and the aforesaid sealing member is made up of: a gas barrier member having high air-tightness for substantially maintaining the degree of reduction in the internal pressure of the blood collecting tube during a period up to blood collection; and a sealing element capable of stopping up the needle hole which might remain after extraction of the hollow needle which has been stuck into the sealing member for blood collection. Accordingly, it is possible to provide a blood collecting tube which does not require any unplugging operation for extracting the plug from the opening of the tubular body when blood is to be collected by means of a needle for testing purposes, thereby realizing easy handling. Also, since the airtightness of the tubular body is maintained during a period from production to use, a hollow needle can be easily stuck through the sealing member, and it is possible to positively assure the liquid-tightness after the hollow needle has been extracted from the sealing member.

15 Claims, 5 Drawing Sheets

BLOOD COLLECTING TUBE

TECHNICAL FIELD

The present invention relates to a blood collecting tube used for blood collection or the like.

BACKGROUND ART

Figure 7:
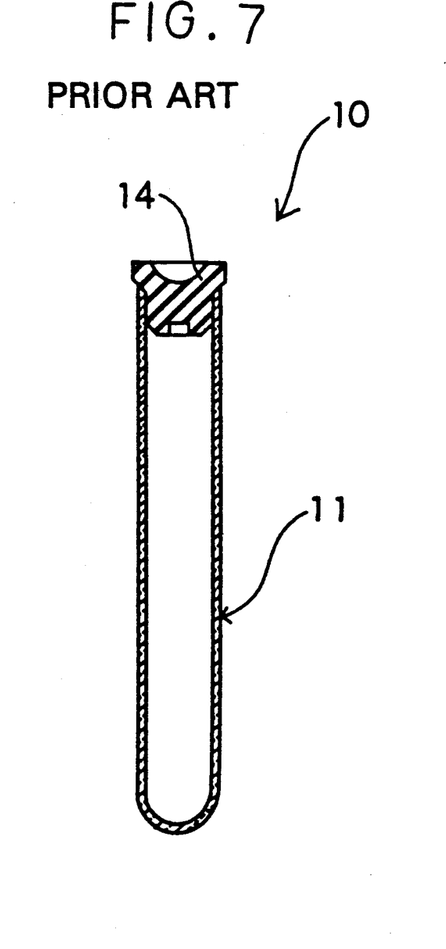
FIG. 7 is a diagrammatic, cross-sectional view of a conventional type of blood collecting and showing the state of the same before use.
Figure 8:
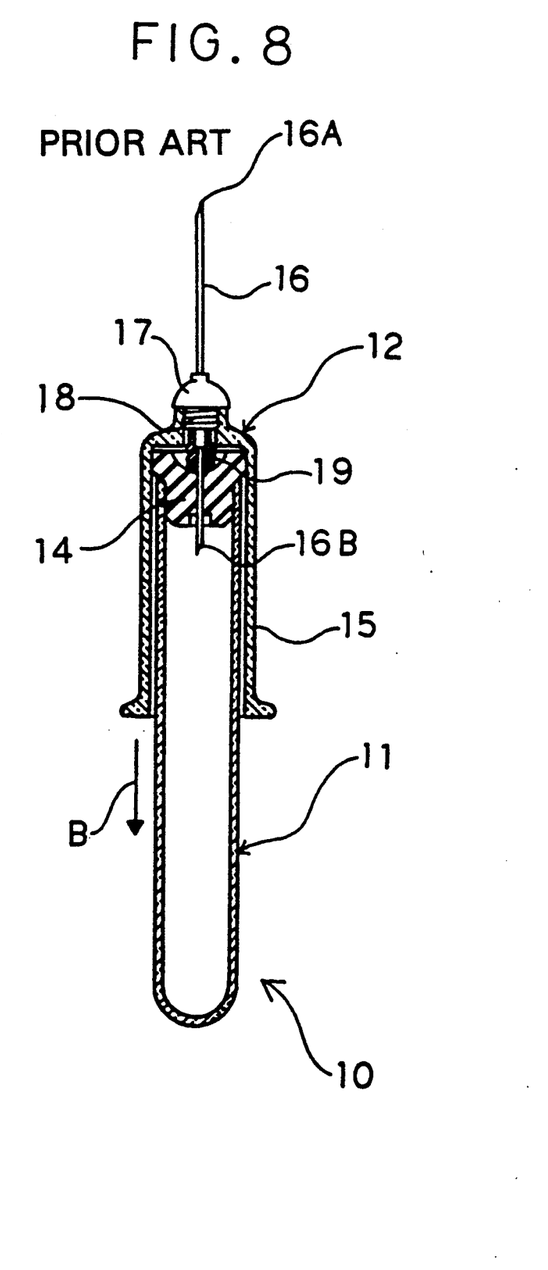
FIG. 8 is a diagrammatic, cross-sectional view of the conventional type of blood collecting tube and showing the sate of the same after use.

A blood collecting tube of the type shown in FIG. 7 has heretofore been used for blood collection which is typically performed in clinical or biochemical testing. FIG. 7 is a cross-sectional view of a conventional type of blood collecting tube before use while FIG. 8 is a cross-sectional view of the same blood collecting tube after use. In the general form of usage, the blood collecting tube is combined with a holder 12 provided with a needle 16 having opposite sharp-pointed ends.

As shown in FIG. 7, s blood collecting tube 10 includes a tubular body 11 and a plug 14 fitted into the opening of the tubular body 11. In general, the tubular body 11 is formed of a material such as glass or a transparent resin, and the plug 14 is made of a rubber material such as vulcanized butyl rubber. The pressure inside the tubular body 11 is maintained in a reduced state. It is possible to stick a hollow needle into the plug 14 as described later and, the addition, it is necessary to maintain the liquid-tightness of the blood collecting tube 10 by stopping up the needle hole which may remain after the hollow needle has been extracted therefrom. In this respect, it has hitherto been considered suitable to use the plug 14 made of a sealing material such as rubber.

On the other hand, a blood collecting holder 12 has a cylindrical holder body 15 which is open at its lower end, and a hollow needle 16 is attached to the upper end portion of the holder body 15. Attachment of the needle 16 is performed by screwing a hub 17 of the needle 16 onto a threaded portion 18 which is formed on the upper end portion of the holder body 15. The forward end 16A of the needle 16 is provided with a sharp-pointed end which is so formed as to pierce the skin while the rearward end 16B of the needle 16 is provided with a sharp-pointed end capable of piercing the plug 14 attached to the tubular body 11. In addition, the rearward end 16B is enclosed in a sheath-like resilient body; for example, a rubber tip 19.

In a case where blood is to be collected using the blood collecting tube 10 and the blood collecting holder 12 each having the aforesaid construction, the forward end 16A of the needle 16 secured to the holder 12 is first stuck into a blood vessel. The blood collecting tube 10 is then inserted into the holder body 15. As shown in FIG. 8, at this time, the needle 16 is stuck through the rubber tip 19 and then into the plug 14 fitted into the blood collecting tube 10, and thus the hollow needle 16 is stuck at its rearward end 16B into the interior of the tubular body 11 having a reduced level of internal pressure. In this state, the rubber tip 19 is collapsed in a bellows-shaped form in the space between the plug 14 and the holder body 15. In consequence, it becomes possible to introduce blood through the forward end 16A of the hollow needle 16 toward the rearward end 16B thereof owing to the fact that the internal pressure of the blood collecting tube 10 is maintained in a reduced state. The thus-introduced blood is allowed to flow into the blood collecting tube 10 and this completes the blood collection.

When a predetermined amount of blood is collected in the interior of the blood collecting tube 10, the blood collecting tube 10 is removed from the holder 12 in the direction indicated by an arrow B (refer to FIG. 8). In this state, the shape of the rubber tip 19 is restored to its original form. If an additional quantity of blood is to be collected, a new tubular body 11 may be inserted into the holder body 15. After completion of the blood collection, the blood collecting holder 12 is removed from the skin.

It is to be noted that the internal pressure of the blood collecting tube 10 is not necessarily be maintained in a reduced state.

In order to take the thus-collected blood out of the blood collecting tube 10 having the aforesaid construction for the purpose of testing, it is necessary to perform an operation termed "unplugging" that is, the plug 14 (such as a rubber plug) needs to be extracted from the opening of the tubular body 11 utilizing a strong force. However, in a case where the plug 14 is formed of a resilient material such as rubber, the operation termed "unplugging" involves various problems; for example, shock which may be produced upon removal of the plug 14 from the tubular body 11 might cause the blood clinging to the tubular body 14 to scatter in the air or to be transferred to the user's hands or the like. There is therefore a strong demand for a solution to this problem. Also, an attempt at extracting blood without removing the plug 14 from the tubular body 11 is made in an automatic testing system. However, even if a needle is to be directly stuck through the plug 14 without removing it from the tubular body 11, the needle is bent due to the large thickness of the rubber plug 14, and this phenomenon makes it difficult to realize such an attempt.

In addition, when the aforesaid blood collecting tube 10 in which the internal pressure is reduced is to be produced in a factory, the pressure within the tubular body 11 is commonly preset at a suitably reduced level in accordance with the amount of blood to be collected. The thus-produced blood collecting tube 10 is commonly stored near the user in a hospital or a doctor's office until it is used. Although the blood collecting tube 10 is stored for a different period by each user, the tube 10 may be stored for as long as 2-3 years. While the blood collecting tube 10 is being stored over such an extended period of time, the air may enter the tube 10 through the portion occupied by the plug 14. In this case, the degree of reduction in the pressure in the blood collecting tube 10 cannot be correctly maintained, and thus, even if such a tube 10 is used in blood collection, it is difficult to collect a predetermined amount of blood. For this reason, in order to assure the air-tightness of the blood collecting tube 10 during storage thereof, various methods have heretofore been considered; for example, the thickness of the plug 14 is increased, or the composition of rubber material is considered. However, if the thickness of the plug 14 is increased, it becomes difficult to stick the needle 16 thereinto, and this may force the operator to do an awkward operation.

Also, the external appearance of the blood collecting tube 10 having the aforesaid plug 14 for the tubular body 11 does not change when putting back the plug 14 in its place after removing it once, and thus, there is a chance using the blood collecting tube 10 whose degree of reduction of the pressure is not correctly maintained for collecting the blood.

It is therefore an object of the present invention to provide a blood collecting tube which is easy to handle without involving the need for a so-called unplugging operation which includes the step of removing the plug from the opening of the tubular body.

It is another object of the present invention to provide a blood collecting tube which is capable of maintaining its air-tightness during the period from production to use and which can be pierced with a hollow needle, as well as being capable of maintaining liquid-tightness even after extraction of the hollow needle.

DISCLOSURE OF INVENTION

To these ends, a blood collecting tube in accordance with the present invention comprises a tubular body which is opened at one end and closed at the other end and a sealing member bonded to the peripheral edge of the opening of the tubular body to seal this opening.

Thus, a feature of the present invention is that the material for and the thickness of the sealing member are selected so as to allow a hollow needle to be stuck through the sealing member.

Another feature of the present invention is that the sealing member is bonded to the tubular body utilizing an adhesive force which allows the sealing member to be peeled from the tubular body if required.

Also, in accordance with the present invention, in a blood collecting tube comprising a tubular body which is opened at one end and closed at the other end and a sealing member which can be pierced by a hollow needle and is bonded to the peripheral edge of the opening of the tubular body to seal the opening in which the internal pressure of the blood collecting tube is suitable reduced in accordance with the amount of blood to be collected, the aforesaid sealing member includes: a gas barrier member having high air-tightness for substantially maintaining the degree of reduction in the internal pressure of the blood collecting tube during a period from production to blood collection; and a sealing element capable of stopping up the needle hole which might remain after extraction of the hollow needle which has been stuck into the sealing member for blood collection.

Thus, a feature of the invention is that the material for and the thickness of the sealing member are selected so as to allow the sealing to be pierced by the hollow needle.

Another feature of the invention is that the sealing member is bonded to the tubular body utilizing an adhesive force which allows the sealing member to be peeled from the tubular body if required.

Another feature of the invention is that the gas barrier member is bonded to the peripheral edge of the opening so that the opening may be completely covered.

Another feature of the invention is that the sealing element having a diameter smaller than that of the gas barrier member is attached to the center of one surface of the gas barrier member.

Another feature of the invention is that the sealing element is deposited over one surface of the gas barrier member.

Another feature of the invention is that the gas barrier is made from aluminum foil film or film coated with vaporized aluminum.

Another feature of the invention is that the sealing element is made of vulcanized rubber.

The other feature of the invention is that the sealing member is integral with a peeling assisting piece which facilitates the peeling of the sealing member from the opening of the tubular body.

BEST MODE FOR CARRYING OUT THE INVENTION

Figure 1:
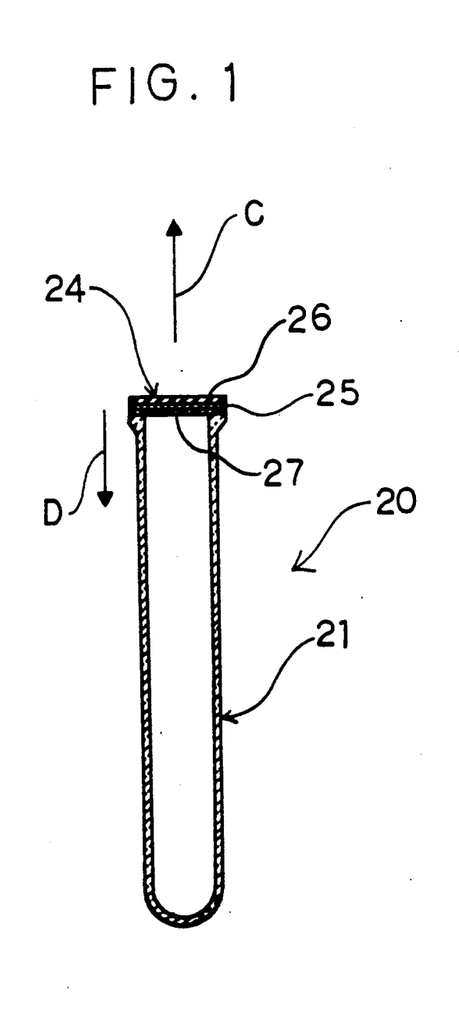
FIG. 1 is a diagrammatic, cross-sectional view of a first preferred embodiment of a blood collecting tube of the present invention and showing the state of the same before use.

As shown in FIG. 1, a blood collecting tube 20 constituting the first preferred embodiment of the present invention includes: a tubular body 21 that is opened at one end and closed at the other end; and a sealing member 24 which allows a hollow needle to be stuck therethrough and which is bonded to the peripheral edge of the opening of the tubular body 21 to seal this opening. The internal pressure of the blood collecting tube 20 is maintained in a reduced state. The tubular body 21 is suitable made of a material which has a high gas-barrier capability, and, from this viewpoint, it is preferable to employ glass, polyvinyl chloride or a polyethylene terephthalate acylic nitrile resin. The tubular body 21 may be formed by a given method such as blow molding, deep drawing molding or vacuum molding. Incidentally, if the tubular body 21 is formed of a material which has a low gas-barrier capability, the external or internal wall of the tubular body 21 is preferable covered with a gas-barrier film of polyvinyl alcohol or polyethylene vinyl alcohol copolymer or the like. If the tubular body 21 is formed of polyvinyl chloride, it is preferable to cover the internal wall of the tubular body 21 with an anti-elution film in order to prevent a stabilizer contained in vinyl chloride from dissolving in collected blood.

In addition, an anti-coagulation agent such as heparin powder, EDTA-2K or the like is included in the internal wall of the closed end portion of the tubular body 21. When blood is allowed to flow into the interior of the tubular body 21, the anti-coagulation agent is capable of dissolving in the blood. It is to be noted that a serum separating agent or a coagulation accelerating agent may be incorporated in the internal wall of the closed end portion of the tubular body 21.

A film-like sealing member 24 attached to the peripheral edge of the upper opening of the tubular body 21 has a highly air-tight gas-barrier member 25 at a lower side thereof and a sealing element 26 over an upper surface thereof, the sealing member 24 being combined with the gas-barrier member 25 in layers in such a manner as to be deposited on each other with the sealing element 26 interposed therebetween. In addition, an adhesive film 27 is deposited on a lower side of the gas-barrier member 25. Specifically, the sealing member 24 is attached to the peripheral edge of the upper opening of the tubular body 21 by bonding the adhesive film 27 to the peripheral edge of such an opening. Incidentally, the gas-barrier member and the sealing element may be positioned upside down. The adhesive film is not necessarily needed, and it is also possible to coat an adhesive on the peripheral edge of the upper opening of the tubular body 21 so as to bond the gas barrier to this opening. Also, the sealing member 24 and the tubular body 21 may respectively be made of materials having mutual solubility, and it is thus possible to attach the sealing member 24 to the peripheral edge of the upper opening of the tubular body 21 by mutually bonding the components 24 and 21 by fusion without using any adhesive. In addition, in order to provide the bonding with a so-called easy peeling prooperty, it is also possible to select a bonding strength which allows the sealing member 24 to be peeled from the upper opening portion such as to enable unplugging thereafter.

The gas-barrier member 25 is preferably made of an material having high air-tightness so that the degree of reduction in the internal pressure of the tubular body 11 may be substantially maintained until the blood collecting tube 20 is used, that is, a needle which will be described later is stuck into the film-like sealing member 24 for the purpose of blood collection. From this viewpoint, the gas-barrier member 25 is made of metal film such as aluminum foil or resin film made of ethylene-vinyl alcohol copolymer, polyvinylidene chloride or the like. It is preferable to use film of aluminum foil or film coated with vaporized aluminum both of which have a good gas-barrier capability. The thickness of the gas-barrier member through which the needle is stuck is 5 to 300 $\mu$m, preferably 20 to 100 $\mu$m, and this thickness is not necessarily uniform. It is preferred that the sealing element 26 be made of a material capable of maintaining the liquid-tightness of the blood collecting tube 20 by stopping up the needle hole which may remain after the blood collecting tube 20 has been used, that is, after a needle which will be described later has been stuck into and extracted from the film-like sealing member 24. From this viewpoint, the sealing element 26 is made of rubber material selected from the group consisting of natural rubber, isoprene rubber, styrenebutadiene rubber, silicone rubber and thermoplastic elastomer. Preferably, vulcanized rubber is selected because of its good sealing characteristic. The thickness of the sealing element through which the needle is stuck is 0.1 to 7 mm, preferably 0.5 to 2 mm.

On the other hand, a blood collecting holder 22 has a cylindrical holder body 29 which is opened at its lower end, and a hollow needle 30 is attached to the upper end portion of the holder body 29. Attachment of the needle 30 is performed by screwing the hub 31 of the needle 30 onto a threaded portion 32 which is formed on the upper end portion of the holder body 29. A forward end 30A of the needle 30 is provided with a sharp-pointed end which is so formed as to pierce the skin while a rearward end 30B of the needle 30 is provided with a sharp-pointed end capable of piercing the film-like sealing member 24 attached to the blood collecting tube 20. In addition, the rearward end 30B is enclosed in a sheath-like resilient body; for example, a rubber tip 33.

Incidentally, in regard to the just-described embodiment, a concrete example of the construction of the blood collecting tube 20 is given below;

Tubular Body:

a polyethylene terephthalate resin is subjected to injection molding to form a tubular body having a volume of 10 cc;

Film-like Sealing Member:

1) The sealing element is made from a sealing sheet made of vulcanized natural rubber;

2) The gas-barrier member is made from a laminated film made up of aluminum foil film (10 $\mu$m) and nylon film (12 $\mu$m); and 3) The adhesive film is made from polyethylene terephthalate film (25 $\mu$m).

1), 2) and 3) are bonded in layers using an epoxy adhesive.

The body of the blood collecting tube is formed by heat-fusing the adhesive film of the film-like sealing member with the peripheral edge of the upper opening of the aforesaid tubular body under a predetermined reduced pressure.

OPERATION OF THE EMBODIMENT

Figure 2:
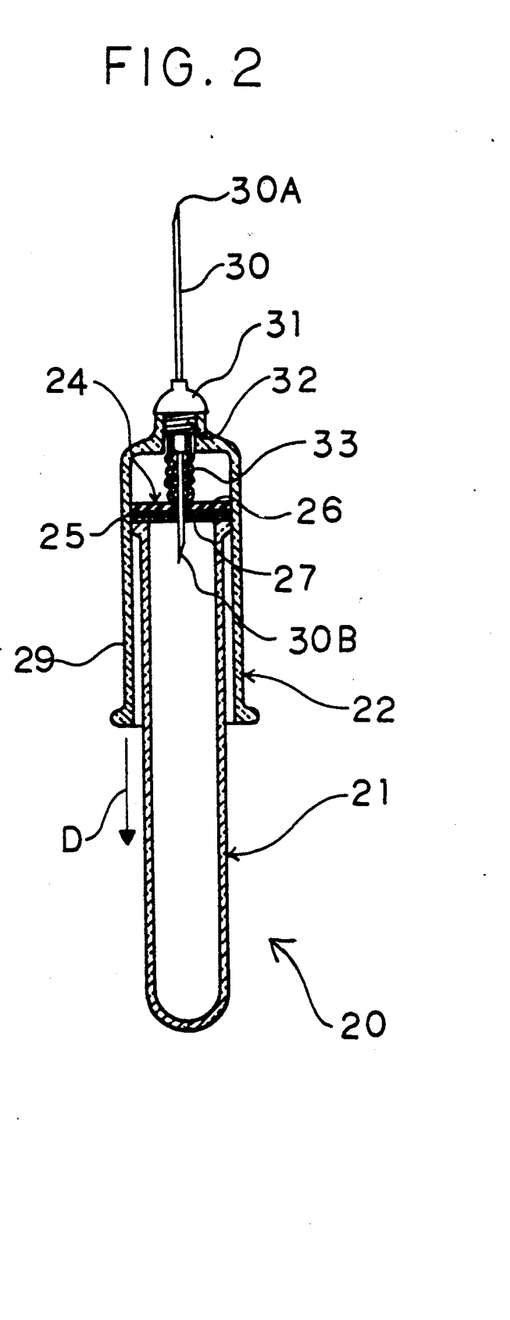
FIG. 2 is a diagrammatic, cross-sectional view of the first embodiment but showing the state of the same after use.
Figure 3:
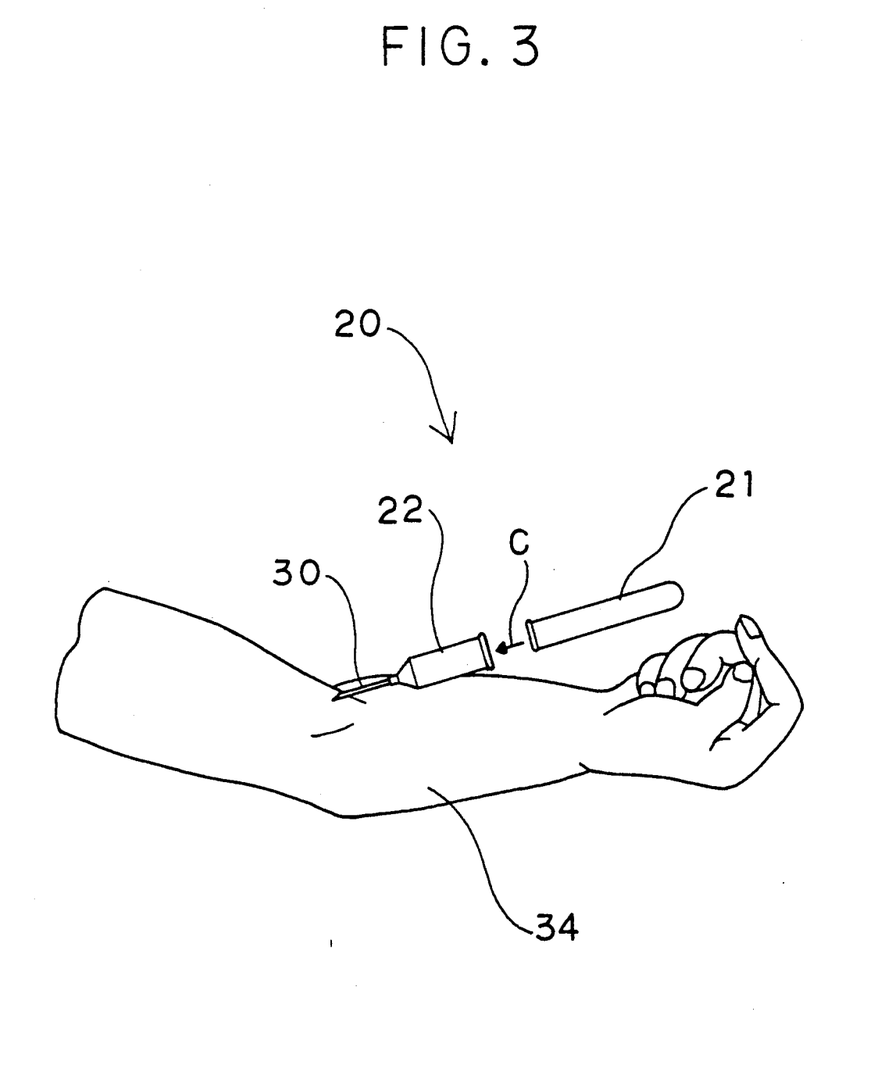
FIG. 3 is a diagrammatic, perspective view of the manner in which blood is collected from an arm of the human body by means of the blood collecting tube of the present invention.

In a case where blood is to be collected using the blood collecting tube 20 having the aforesaid construction, the forward end 30A of the needle 30 secured to the blood collecting holder 22 is first stuck into the skin of an arm, as shown, for example, in FIG. 3. The blood collecting tube 20 is then inserted into the holder body 29 in the direction indicated by an arrow C. As shown in FIG. 2, at this time, the needle 30 is stuck through the rubber tip 33 and then into the film-like sealing member 24 fitted into the blood collecting tube 20, and thus the hollow needle 30 is stuck at its rearward end 30B into the interior of the tubular body 21 having a reduced internal pressure. In this state, the rubber tip 33 is collapsed in a bellows-shaped form in the space between the film-like sealing member 24 and the holder body 29. In consequence, it becomes possible to introduce blood through the forward end 30A of the hollow needle 30 toward the rearward end 30B thereof owing to the fact that the internal pressure of the tubular body 21 is maintained in a reduced state. The thus-introduced blood is allowed to flow into the tubular body 21 and this completes the blood collection.

When a predetermined amount of blood is collected in the interior of the tubular body 21, the blood collecting tube 20 is removed from the blood collecting holder 22 in the direction indicated by an arrow D. In this state, the shape of the rubber tip 33 is restored to its original form owing to the resiliency of the rubber. If an additional quantity of blood is to be collected, a new tubular body 11 may be inserted into the holder body 15. After completion of the blood collection, the blood collecting holder 12 is removed from the arm 34.

Since the gas barrier member 25 is present in the film-like sealing member 24, the blood collecting tube 20 having the aforesaid construction is capable of maintaining its air-tightness during a period from production to use. Also, the presence of the sealing element 26 positively enables the sealing member 24 to assure the liquid-tightness after the needle 30 has been stuck into and removed from the sealing member 24. In addition, the presence of the gas barrier 25 eliminates the need to increase the thickness of the sealing element 26 which was previously required to maintain the reduced state of internal pressure, and thus the needle is readily stuck into the film-like sealing member 24. Also, since the thickness of the sealing element 26 can be decreased, it is possible to stick the needle of an automatic serum sampler directly through the sealing member 24. Therefore, after blood collection followed by centrifugation, the blood collecting tube 20 can be set directly in the automatic serum sampler without the need to peel the sealing member 24 from the opening portion of the tubular body 21, thereby enabling serum sampling.

Also, since the sealing member 24 is bonded on the opening portion of the tubular body 21, thereby the aforesaid blood collecting tube 20 is easily distinguishable from a one whose degree of reduction of the pressure is deteriorated after opening the sealing member once.

In the aforesaid embodiment, since the sealing element 26 is deposited over the upper surface of the gas barrier member 25, it is possible to prevent the film-like gas barrier member 25 from being broken by the force which is applied to the member 25 when the needle 30 is stuck into the sealing member 24.

In addition, in the aforesaid embodiment, since the gas barrier member 25 is intimately bonded to the peripheral edge of the opening of the tubular member 21 via the adhesive film 27, the pressure within the tube is maintained in a reduced state after blood has been collected, and thus it is possible to completely prevent the contamination of the collected blood.

It is to be noted that there is a likelihood that the aforesaid embodiment may involve the phenomenon called "kick back" in which, during blood collection, the tubular body 21 is pushed out of the blood collecting holder 22 due to the resiliency of the rubber tip 33 incorporated in the holder 22. To obviate this problem, a projection may be formed on the periphery of the opening of the tubular body 21 while a corresponding groove may be formed on the internal wall of the holder body 29 such that the projection and the groove may be engaged with each other during a blood collecting operation.

ANOTHER EMBODIMENT

Figure 4:
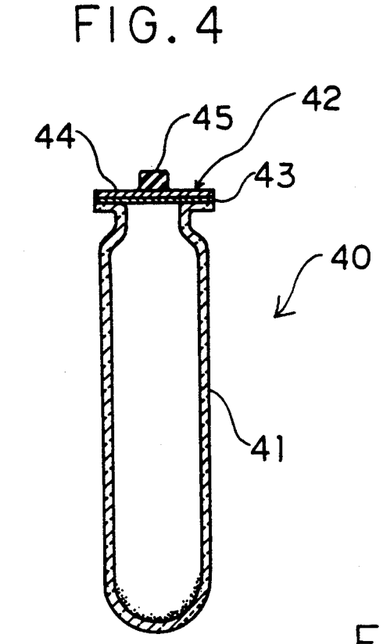
FIG. 4 is a diagrammatic, cross-sectional view of a second preferred embodiment of a blood collecting tube of the present invention and showing the state of the same before use.

FIG. 4 is a diagrammatic, cross-sectional view of a second preferred embodiment of the blood collecting tube of the present invention but showing the state of such a tube before use.

A blood collecting tube 40 has a tubular body 41, and a sealing member 42 is attached to the peripheral edge of the upper opening of the tubular body 41. The tubular body 41 is formed by blow molding using an acrylic nitrile resin such as that known under the tradename Barex 210 (manufactured by Mitsui Toatsu Kabushiki Kaisha), and the inner wall of the tubular body 41 is coated with water-soluble silicone used for preventing the adhesion of blood clots such as that known under the tradename SF8421 (manufactured by Torei Silicone Kabushiki Kaisha) which is also used in the treatment of a conventional type of vulcanized rubber plug. Glass powder (5 mg) as a coagulation accelerating medium is stuck to the internal wall of the closed end portion of the tubular body 41.

The sealing member 42 is intimately bonded to the peripheral edge of the opening of the tubular body 41 using adhesive film 43 having a thickness of 25 $\mu$m such as that known under the tradename Barex 210 Film (manufactured by Mitsui Toatsu Kabushiki Kaisha). The sealing member 42 includes a gas barrier member 44 (12-$\mu$m-thick polyethylene terephthalate film coated with vaporized aluminum) which is provided on the upper surface of the adhesive film 43, and a sealing element 45 (1.2mm-thick vulcanized natural rubber) which is attached to the gas barrier member 44. The gas barrier member 44 is in advance bonded to the adhesive film 43 using an epoxy adhesive and, in addition, the sealing element 45 is bonded to the upper surface of the gas barrier member 44 using rubber paste. In other words, the sealing element 45 is not necessarily be deposited over the upper surface of the gas barrier member 44 in the same manner as that shown in the first preferred embodiment. The sealing element 45 having a smaller diameter than that of the gas barrier member 44 may be disposed at the central portion of the gas barrier 44 to be pierced by the needle 30.

Figure 5:
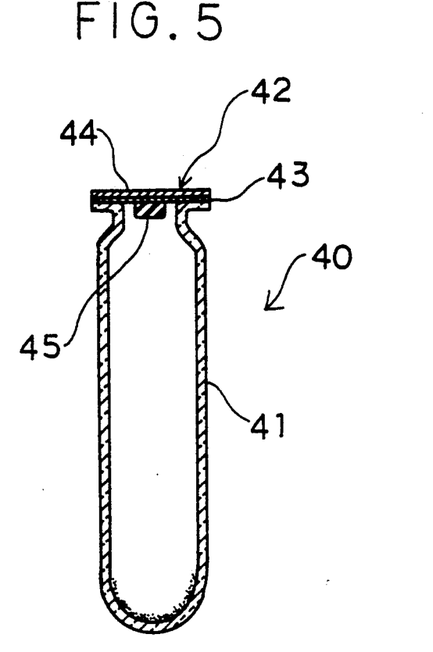
FIG. 5 is a diagrammatic, cross-sectional view of one modification of the second embodiment shown in FIG. 4.

As shown in FIG. 5 as a modified form, the sealing element 45 may be attached to the central portion of the lower surface of the adhesive film 43.

As in the case of the sealing member 42 shown in FIGS. 4 and 5, if the sealing element 45 has a diameter smaller than that of the gas barrier member 44, for example, a diameter equivalent to half of the diameter of the opening of the tubular body 41, and is attached to the central portion of the gas barrier member 44, the needle of an automatic tester may be stuck through the ring-shaped portion of the gas barrier member 44 devoid of the sealing element 45 so as to draw blood therefrom. Resistance to sticking is smaller in this case than in the case where the needle of the automatic tester is stuck through the sealing element 45. In this case, since the needle is not passed through the sealing element 45, it is possible to ventilate the tubular body 41 through the gap between the needle and the needle hole of the gas barrier member 44 in which the needle is inserted. Thus, if blood is drawn out of the blood collecting tube, the pressure within the blood collecting tube does not become negative, that is, it is possible to smoothly perform an blood drawing operation.

Figure 6:
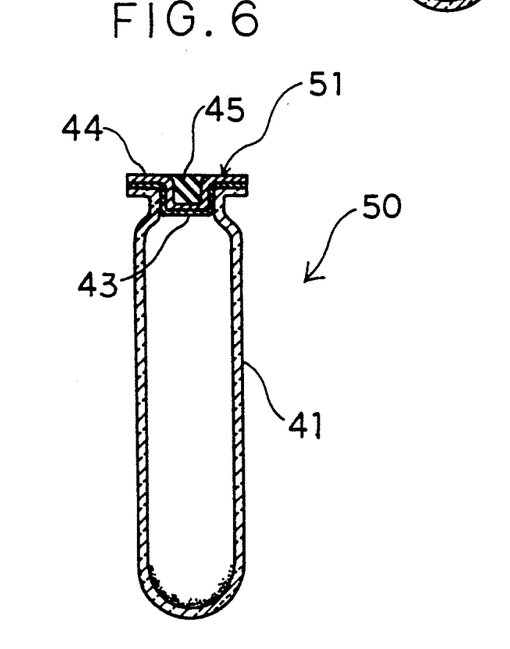
FIG. 6 is a diagrammatic, cross-sectional view of a third preferred embodiment of a blood collecting tube of the present invention and showing the state of the same before use.

FIG. 6 is a diagrammatic, cross-sectional view of a third preferred embodiment of the blood collecting tube of the present invention and showing the state of such a tube before use.

A blood collecting tube 50 has the tubular body 41 which is constructed in the same manner as that of the aforesaid second embodiment, and a sealing member 51 formed by deep drawing molding is fitted into the opening of the tubular body 41. The sealing member 51 includes the sealing element 45 attached to the central portion of the uppoer surface of the gas barrier member 44 bonded to the adhesive film 43, and is formed by deep drawing molding so as to have a downwardly projecting portion which should be inserted into the opening of the tubular body 41. In addition, the surface of the adhesive film 43 which comes into contact with blood is preferably coated with water-soluble silicone used for preventing the adhesion of blood clots. This coating does not adversely affect the bonding strength of the film 43.

If the sealing member is made up of a gas barrier member and a sealing element, the gas barrier member and the sealing element are not necessarily bonded to each other.

The present invention further embraces another modified form of the sealing member which is bonded to the peripheral edge of the opening of the tubular body for sealing purposes but which does not necessarily have a gas berrier function for high air-tightness. The following is a description of such a modified form of the present invention.

Blood serum for biochemical testing has heretofore been prepared by collecting blood using a vacuum blood collecting tube, subjecting the blood to centrifugation after coagulation, removing a plug from a tubular body, sampling blood serum using a pippet and transferring the serum to a sampling container or by collecting serum into the sampling container by means of an automatic serum sampler. In order to prevent the evaporation of water, a simple cap made of plastics may be fitted onto the container or sealing film may be wrapped around the same. During the aforesaid operation, the container may remain open, and this is disadvantageous in terms of the prevention of contamination with respect to the serum. To solve this problem, it is possible to employ the previously described blood collecting tube of the invention. In this case, the blood collecting tube does not necessarily need the gas berrier function such as that of the aforesaid embodiment, and thus can be employed without the need to maintain the internal pressure thereof in a reduced state. More specifically, in acoordance with this modified form, the blood collecting tube is used as the aforesaid sampling container of an utomatic serum sampler. More specifically, after blood has been collected into a vacvuum blood collecting tube which is separately prepared, the blood is sampled from such a vacvuum blood collecting tube by means of the automatic serum sampler. The thus-sampled blood is introduced into the sampling container via a needle which is stuck into its film-like sealing member. In this case, a pneumatic needle may preferable be stuck through the film-like sealing member in order to prevent an increase in the pressure within the container. The container includes a container body and a film-like sealing member, and is constructed in substantially the same manner as shown in FIG. 1. The construction of this modified form differs from that depicted in FIG. 1 merely in that another substance having no gas barrier property can be used instead of the gas barrier member shown in FIG. 1. The container body may be made of glass or plastics. The plastics may be selected from the group consisting of polypropylene, polyethylene, polystyrene, polymethyl methacrylate, polyvinyl chloride, polyethylene terephthalate, AS resins, ABS resins, polycarbonate and ethylene vinyl acetate copolymers. The film-like sealing member requires a "resealing" property in which, after an injecting needle has been extracted therefrom, even if the container is placed upside down, the liquid content is not allowed to flow through the pore of the sealing member which is formed by the needle. This is achieved, for example, by thermoplastic elastomer laminated on polyester film. The average thickness of the film-like sealing member is preferably equal to or less than 1 mm. A sealant is coated over the surface of the film-like sealing member which is bonded to the container body, and this provide sealing for the body. Of course, this sealing is also enabled by using the same material as that of the body. The following is a description of one example of this modified form.

EXAMPLE OF MODIFIED FORM

A container body was formed of polystyrene (sold under the tradename Estylene G-12; manufactured by Nippon Steel Chemical Kabushiki Kaisha). A film-like sealing member included a heat sealant (sold under the tradename Latiseal A7734A, manufactured by Cemedyne Kabushiki Kaisha) which was coated over 12-$\mu$m-thick polyester film and, in addition, SEBS-based thermoplastic elastomer (under the tradename Rabalon SJ5400, manufactured by Mitsubishi Petrochemical Co., Ltd.) which was laminated to form a 5-mm-thick layer on the latter. A 21-G pneumatic needle was stuck into the film-like sealing member and thus serum was extracted from the container body via the 21-G needle. After the needle had been drawn out of the container, even if the container was placed upside down, the liquid content was not allowed to flow out of the container. With this modified form, a blood sample can be transferred from one to another container with the container maintained in a hermetically sealed state, and this reduce the risk of blood being contaminated. In particular, this modified form is effectively used with an automatic serum sampler. Also, when blood is to be collected via a needle for testing purposes, this modified form of blood collecting tube requires no unplugging operation for extracting a plug from the opening of the tubular body, and it is thus easy to handle the modified form.

Since the sealing member is incorporated, the interior of the blood collecting tube is prevented from being contaminated by volatile matter as in the case of a rubber plug, thereby maintaining the interior in a clean state.

In the aforedescribed embodiments, the sealing member is bonded to the peripheral edge of the opening of the tubular body via an adhesive layer. However, in some of the embodiments, the sealing member may be bonded directly to the peripheral edge of the opening (for example, the sealing member and the tubular body may be formed of the same material to be bonded to each other by ultrasonic fusion).

Also, while the blood collecting tube of the invention is being used, the sealing member may be peeled from the tubular body as required when blood is to be sampled for testing purposes. Since this pealing does not involve the shock that might be experienced with a rubber plug, the blood clinging to the plug is not scattered. In addition, the blood collecting tube of the invention may be integral with a pealing assisting piece in order to facilitate the aforesaid peeling of the sealing member.

INDUSTRIAL APPLICABILITY

As described above, the blood collecting tube of the present invention includes the tubular body that is opened at one end and closed at the other end and the sealing member which is bonded to the peripheral edge of the opening of the tubular body so as to seal this opening. Accordingly, when blood is to be collected for testing purposes, an unplugging operation for extracting the plug from the opening of the tubular body is not needed, thereby facilitating the handling of the blood collecting tube.

Also, since the sealing member is bonded on the opening portion of the tubular body, thereby the aforesaid blood collecting tube is easily distinguishable from a one whose degree of reduction of the pressure is deteriorated after opening the sealing member once.

In accordance with the present invention, since the material for and the thickness of the sealing member are selected so that the sealing member may allow a hollow needle to be stuck therethrough, the aforesaid operation for sticking the hollow needle can be performed positively and easily.

In accordance with the present invention, since the sealing member is bonded utilizing an adhesive force which allows member to be peeled if required, while blood is being collected for testing purposes, it is possible to prevent the scattering of blood which might be experienced with a rubber plug.

The blood collecting tube of the present invention comprises a tubular body that is opened at one end and is closed at the other end and a sealing member which can be pierced by a hollow needle and is bonded to the peripheral edge of the opening of the tubular body to seal this opening in which the internal pressure of the tubular body is suitably reduced in accordance with the amount of blood to be collected, and the aforesaid sealing member is made up of: a gas barrier member having high air-tightness for substantially maintaining the degree of reduction in the internal pressure of the blood collecting tube during a period up to blood collection; and a sealing element capable of stopping up the needle hole which might remain after extraction of the hollow needle which has been stuck into the sealing member for blood collection. Accordingly, if blood is to be collected by means of a needle for testing purposes, an unplugging operation for extracting the plug from the opening of the tubular body is not required, thus facilitating the handling of the blood collecting tube. Also, since the airtightness of the tubular body is maintained during a period from production to use, a hollow needle can be easily stuck through the sealing member, and it is possible to positively assure the liquid-tightness after the hollow needle has been extracted from the sealing member.

In accordance with the present invention, since the material for and the thickness of the sealing member are selected so that the sealing member may allow a hollow needle to be stuck therethrough, the aforesaid operation for sticking the hollow needle can be positively and easily performed without involving the risk of the sealing member being broken by the hollow needle stuck through the sealing member.

In accordance with the present invention, since the sealing member is bonded utilizing an adhesive force which allows the member to be peeled if required, while blood is being collected for testing purposes, it is possible to prevent the scattering of blood whick might be experienced with a rubber plug.

In accordance with the present invention, since the gas barrier is bonded to the peripheral edge of the opening of the tubular member so as to completely cover this opening, the degree of reduction in the internal pressure of the blood collecting tube can be positively maintained at a sufficient level.

In accordance with the present invention, since the sealing element has a diameter smaller than that of the gas barrier member and is attached to the center portion of the gas barrier member, the needle of an automatic tester may be stuck through the portion of the gas barrier member that is devoid of the sealing element, thereby facilitating blood collecting operation.

In accordance with the present invention, since the sealing element is deposited over the surface of the gas barrier member, it is possible to prevent the gas barrier member from being broken by the force applied to the gas barrier member when a hollow needle is stuck thereinto.

In accordance with the present invention, since the aforesaid gas barrier is made from aluminum foil film or film coated with vaporized aluminum, the airtightness of the blood collecting tube can be positively assured at a sufficient level during a period from production to use.

In accordance with the present invention, since the sealing member is made of vulcanized rubber, the liquid-tightness can be positively assured at a sufficient level after the hollow needle has been extracted from the sealing member.

In addition, in accordance with the present invention, since the sealing member is integral with a peeling assisting piece for facilitating the peeling of the sealing member from the opening of the tubular member, it is possible to facilitate the operation for peeling the seeling member which may be performed if required.

What is claimed is:

1. A blood collecting tube, comprising:
   a tubular body which is open at one end and closed at the other end, said open end having a peripheral edge at the opening thereof;
   a sealing member having a material construction and thickness so as to be pierceable by a hollow needle, and said sealing member being removably bonded to said peripheral edge of said opening of said tubular body by adhesive means for sealing said opening and for maintaining a reduced internal pressure within said blood collecting tube in accordance with an amount of blood to be collected;
   said sealing member including:
   a gas barrier member having a high degree of air-tightness for covering said opening of said tubular body and for substantially maintaining said reduced internal pressure within said blood collecting tube during a period from production to blood collection, said gas barrier member being removably bonded to said peripheral edge of said opening by said adhesive means such that said opening of said tubular body is completely covered; and
   a sealing element on a surface of said gas barrier member, said sealing element being capable of stopping up a needle hole which might remain after extraction of a hollow needle which has been stuck into and which has pierced said sealing member for blood collection; and
   said sealing member being bonded to said peripheral edge of said opening of said tubular body by said adhesive means such that the adhesive force of said adhesive means allows said sealing member to be selectively peeled from said peripheral edge of said tubular body substantially without producing impact or shock, thereby preventing scattering of blood during removal of said sealing member.

2. The blood collecting tube of claim 1, wherein said sealing element has a diameter smaller than that of said gas barrier member and is attached to a central portion of one surface of said gas barrier member.

3. The blood collecting tube of claim 1, wherein said sealing element is deposited over at least a portion of one surface of said gas barrier member.

4. The blood collecting tube of claim 1, wherein said gas barrier member comprises an aluminum foil film.

5. The blood collecting tube of claim 1, wherein said gas barrier member comprises a film coated with vaporized aluminum.

6. The blood collecting tube of claim 1, wherein said sealing element is made of vulcanized rubber.

7. The blood collecting tube of claim 6, wherein said sealing element comprises a layer of said vulcanized rubber on at least a portion of a surface of said gas barrier member.

8. The blood collecting tube of claim 1, wherein said sealing member comprises an integrally formed peeling assisting member which facilitates a peeling of said sealing member from said opening of said tubular body.

9. The blood collecting tube of claim 1, wherein said adhesive means comprises an adhesive layer on a lower side of said gas barrier member.

10. The blood collecting tube of claim 9, wherein said sealing element is on an outer surface of said gas barrier member, whereby said gas barrier member is interposed between said adhesive layer and said sealing element.

11. The blood collecting tube of claim 1, wherein said gas barrier member comprises an air-tight layer for covering said opening of said tubular body, and wherein said sealing element comprises a layer on an outer surface of said gas barrier member.

12. The blood collecting tube of claim 11, wherein said adhesive means comprises an adhesive layer on a lower surface of said gas barrier layer which contacts said peripheral edge of said opening.

13. The blood collecting tube of claim 12, wherein said sealing layer is vulcanized rubber.

14. The blood collecting tube of claim 13, wherein said gas barrier layer comprises an aluminum foil film.

15. The blood collecting tube of claim 12, wherein said gas barrier layer comprises a film coated with vaporized aluminum.

* * * * *